United States Patent
Bol'shakova et al.

(10) Patent No.: US 10,603,338 B2
(45) Date of Patent: Mar. 31, 2020

(54) METHOD FOR POLY SIGNAL ACTIVATION OF APOPTOSIS OF MALIGNANT SOLID TUMOUR CELLS

(71) Applicant: OBSHESTVO S OGRANICHENNOI OTVETSTVENNOST'YU "BIOTEHNOLOGIYA", Moscow (RU)

(72) Inventors: Tat'yana Nikolaevna Bol'shakova, Moscow (RU); Ekaterina Feodorovna Kolesanova, Vniissok (RU); Ekaterina Ur'evna Rybalkina, Moscow (RU); Igor' Gennad'evich Sivov, Moscow (RU)

(73) Assignee: OBSHESTVO S ORGANICHENNOI OTVETSTVENNOST'YU "BIOTEHNOLOGIYA", Moscow (RU)

( * ) Notice: Subject to any disclaimer, the term of this patent is extended or adjusted under 35 U.S.C. 154(b) by 12 days.

(21) Appl. No.: 15/757,285

(22) PCT Filed: Oct. 21, 2016

(86) PCT No.: PCT/RU2016/000722
§ 371 (c)(1),
(2) Date: Mar. 2, 2018

(87) PCT Pub. No.: WO2017/052419
PCT Pub. Date: Mar. 30, 2017

(65) Prior Publication Data
US 2018/0250331 A1 Sep. 6, 2018

(30) Foreign Application Priority Data
Sep. 22, 2015 (RU) ................................ 2015140255

(51) Int. Cl.
| | | |
|---|---|---|
| *A61K 33/24* | (2019.01) | |
| *A61K 47/64* | (2017.01) | |
| *A61K 47/69* | (2017.01) | |
| *A61K 47/46* | (2006.01) | |

(52) U.S. Cl.
CPC .............. *A61K 33/24* (2013.01); *A61K 47/46* (2013.01); *A61K 47/64* (2017.08); *A61K 47/6901* (2017.08)

(58) Field of Classification Search
None
See application file for complete search history.

(56) References Cited

U.S. PATENT DOCUMENTS

2013/0017210 A1* 1/2013 Peabody .............. C07K 16/005
424/178.1
2013/0251630 A1* 9/2013 Petersen ............ A61K 51/1234
424/1.21

OTHER PUBLICATIONS

Chia et al., "Thallium Acetate Induces C6 Glioma Cell Apoptosis", 2005, Ann. N.Y. Acad. Sci., vol. 1042, pp. 523-530.*
Jin et al., "Targeted Delivery System of Nanobiomaterials in Anticancer Therapy: From Cells to Clinics", 2014, BioMed Research International, pp. 1-23.*
Zhou et al., "Octa-functional PLGA nanoparticles for targeted and efficient delivery to tumors", 2012, Biomaterials, vol. 33, pp. 583-591.*
Chia CF, et al., Thallium acetate induces C6 glioma cell apoptosis. Ann NY Acad Sci. May 2005;1042:523-30.
Rodríguez-Mercado, et al., Evaluation of cytogenetic and DNA damage caused by thallium(I) acetate in human blood cells. Environ Toxicol. May 2015;30(5):572-80.
Capehart SL, et al., Controlled integration of gold nanoparticles and organic fluorophores using synthetically modified MS2 viral capsids. J Am Chem Soc. Feb. 27, 2013;135(8):30.
Karimi M, et al., Bacteriophages and phage-inspired nanocarriers for targeted delivery of therapeutic cargos. Adv Drug Deliv Rev. Nov. 15, 2016;106(Pt A):45-62.
Zhang, et al., Encapsulation of Inorganic Nanomaterials inside Virus-Based Nanoparticles for Bioimaging. Nanotheranostics. Aug. 18, 2017;1(4):358-368.

* cited by examiner

*Primary Examiner* — Robert A Wax
*Assistant Examiner* — Randeep Singh
(74) *Attorney, Agent, or Firm* — Dmitry S. Kryndushkin

(57) ABSTRACT

A method is provided for the poly signal activation of apoptosis of malignant solid tumour cells, carried out by means of the targeted delivery of thallium salts by surface-modified MS2 phage virions, which contain a cyclic iRGD ligand that has a high affinity for the integrins avb3 and avb5 and is covalently bound with the shell and with the core, which contains genomic RNA and thallium salts. Complex, efficient, prolonged cytotoxic action is provided on focal and metastatic clusters of malignant solid tumour cells, while minimizing undesirable side effects on the healthy cells of an organism.

4 Claims, 6 Drawing Sheets

METHOD FOR POLY SIGNAL ACTIVATION OF APOPTOSIS OF MALIGNANT SOLID TUMOUR CELLS

CROSS-REFERENCE TO RELATED APPLICATION

Figure 1:
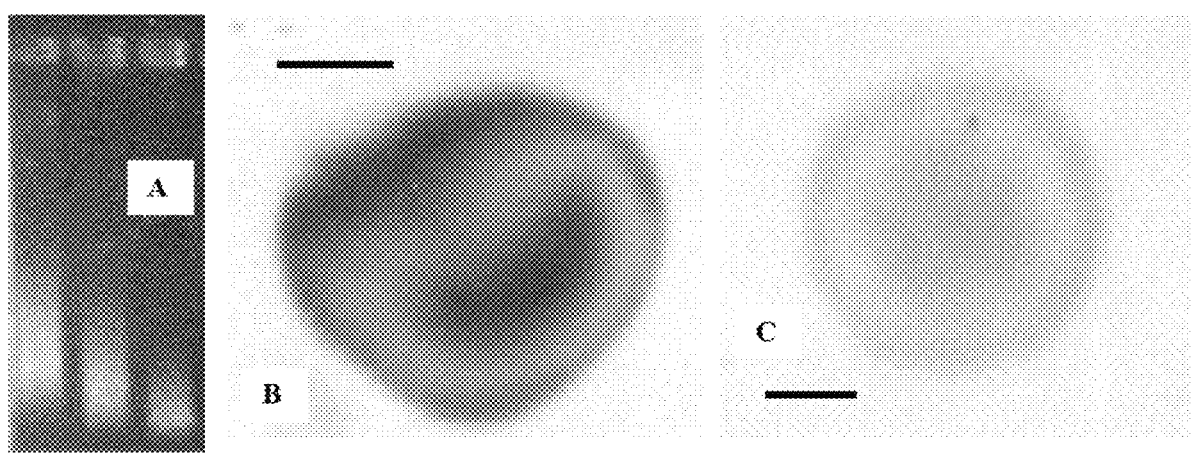
Figure 2:
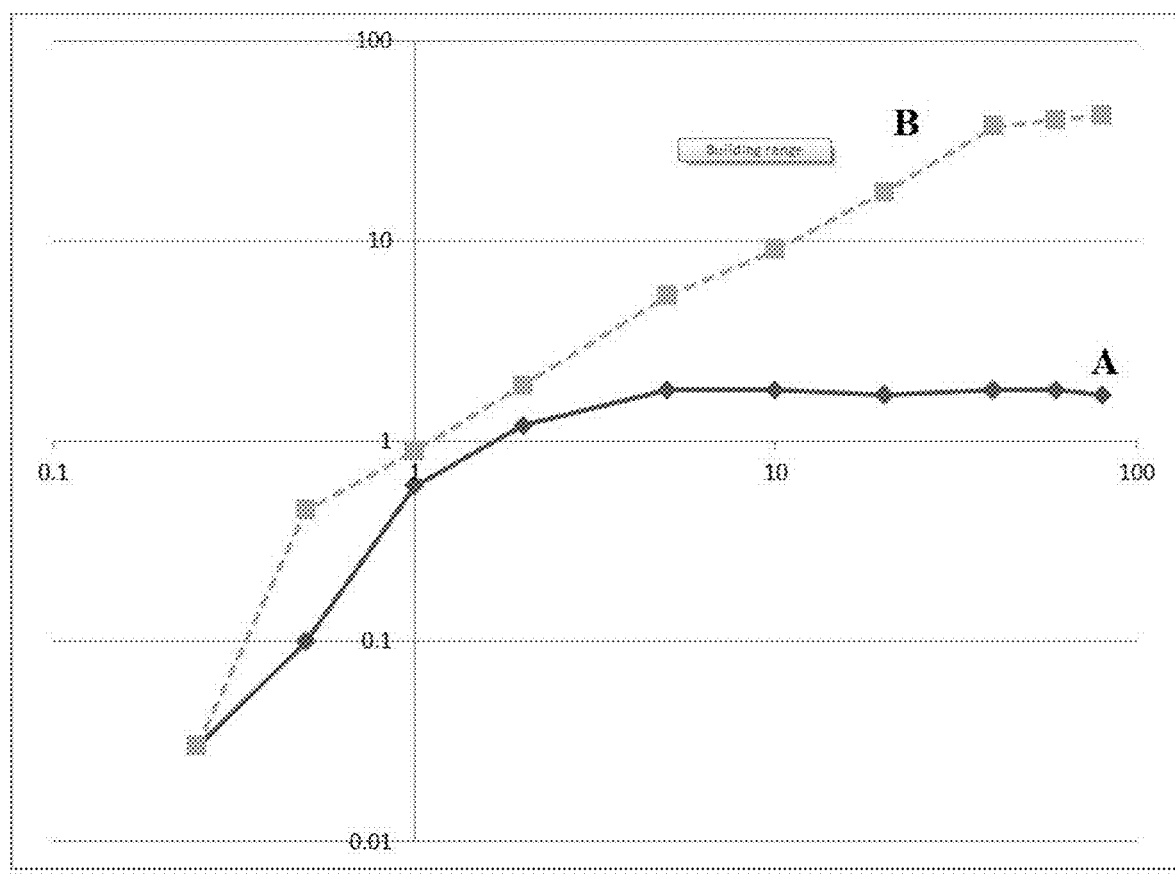
Figure 3:
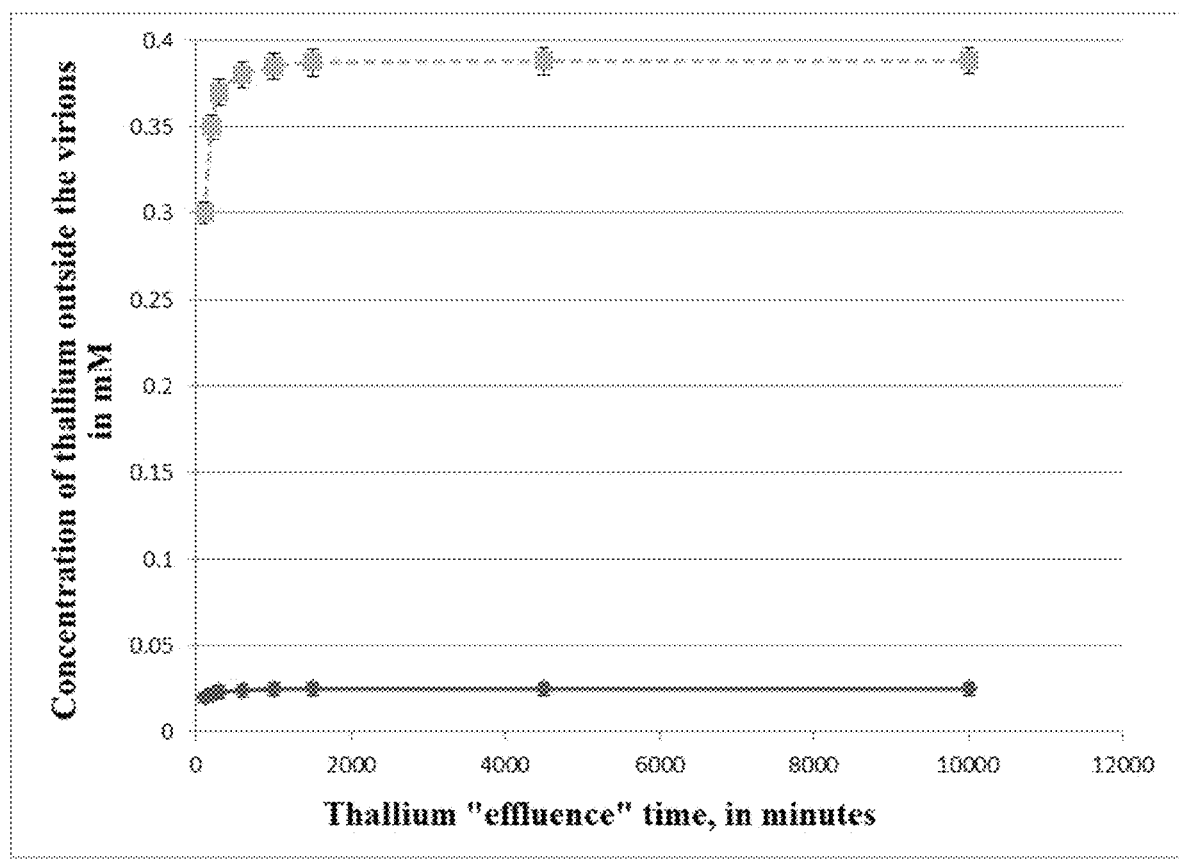
Figure 4:
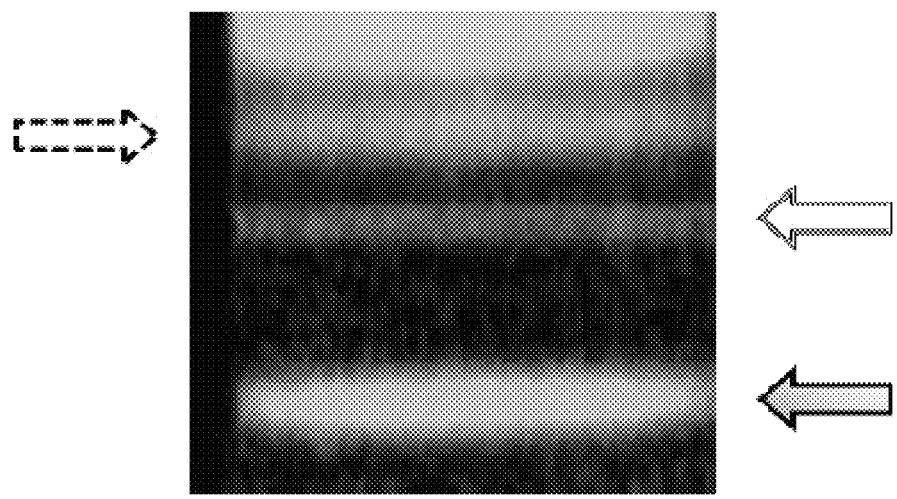
Figure 5:
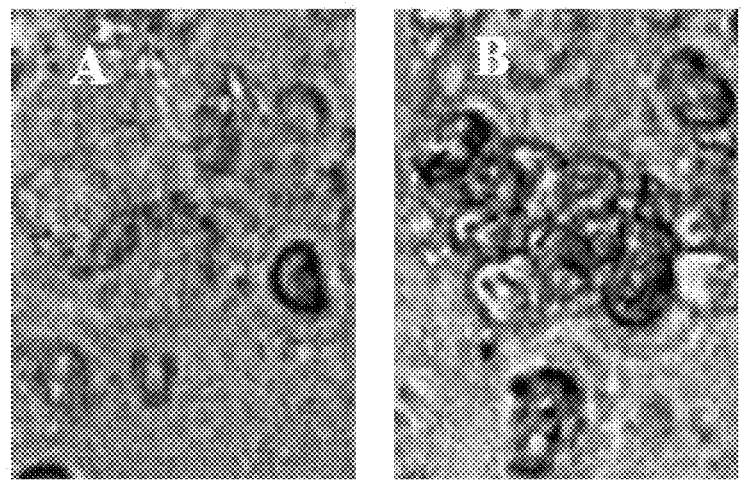
Figure 6:
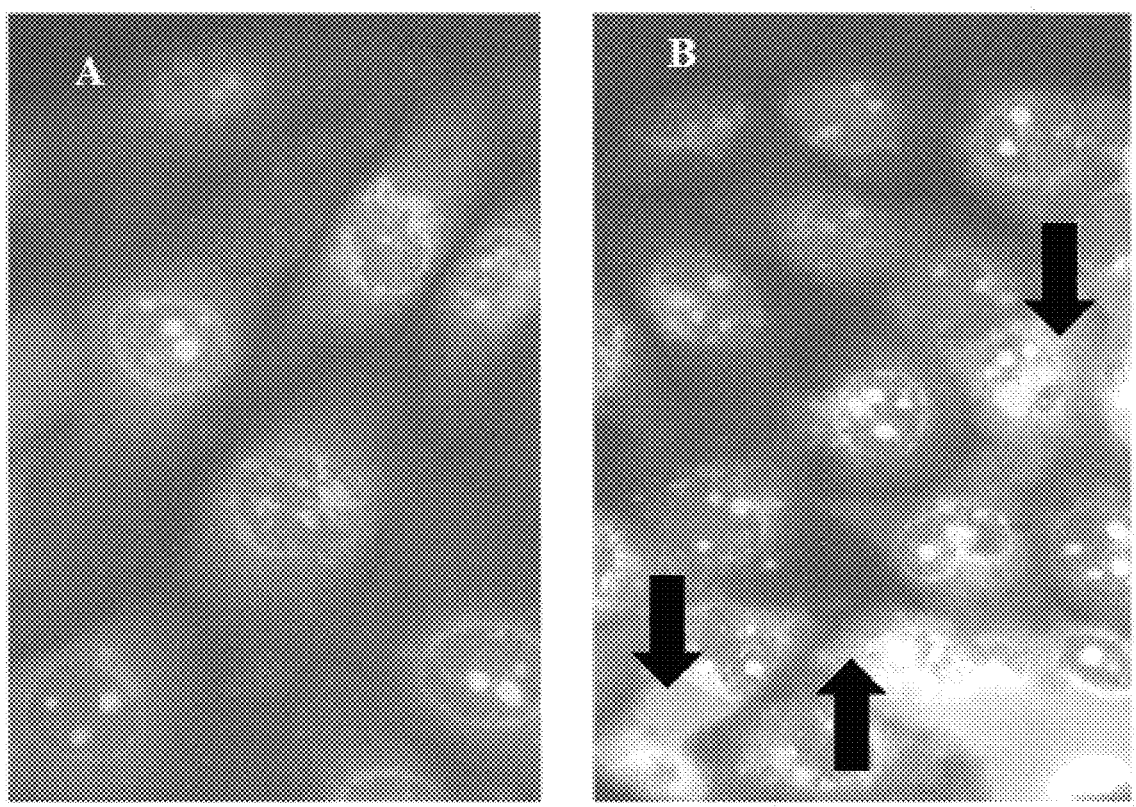

The instant application is a national phase of PCT International Application No. PCT/RU2016/000722 filed Oct. 21, 2016, and claims priority to Russian Patent Application Serial No. 2015140255 filed Sep. 22, 2015, the entire specifications of both of which are expressly incorporated herein by reference.

FIELD OF THE INVENTION

This invention relates to targeted chemotherapy suitable for delivery of thallium salts to focal and metastatic accumulations of cells of malignant solid tumors (MSTs). And more specifically to obtaining and using bacteriophage modified with ligand in order to deliver salts of univalent thallium, which induces apoptosis of the cells and which is not removed from the cells by drug resistance protein pumps, for the following therapeutic purposes. The matters, substances and ways described herein will find their application when curing and/or preventing MSTs.

BACKGROUND OF THE INVENTION

At present, humanized antibody preparations are used for targeted chemotherapy of tumors in the Russian Federation (Gain A. M., Bazin I. S. Targeted Therapy of Solid Tumors. A Handbook for Clinician Oncologists. Moscow, 2009).

However, other systems of targeted delivery of various chemotherapeutic agents, which, as a rule, are highly toxic, to tumor cells are intensely devised (US Patent Application 20090047318, 20130287853). Chemotherapeutic agents are incapsulated, for example, into virus-like particles (U.S. Pat. No. 8,324,149, US Patent Application 20080274905) or into virions of RNA-containing bacteriophages (U.S. Pat. Nos. 5,677,124, 6,159,728, US Patent Application 20100167981; Carlee E. Ashley et al. Cell-Specific Delivery of Diverse Cargos by Bacteriophage MS2 Virus-Like Particles//ACS Nano. 2011 Jul. 26; 5(7): 5729-5745 and Jeff E. Glasgowa et al. Osmolyte-Mediated Encapsulation of Proteins inside MS2 Viral Capsids//ACS Nano. 2012 Oct. 23; 6(10): 8658-8664; the abbreviation ACS means the American Chemical Society). By virtue of such an approach, the idea of guaranteed destruction of the MST cells with simultaneously decreasing the exposure of all the organism to the toxic preparations is implemented.

Attention to RNA-containing bacteriophages, to MS2 in particular, as to a means of the targeted delivery, is explained by the simplicity of the virion organization and by absence of receptors specific to it on the surface of human and mammal cells, which excludes its penetration into a cell of these organisms. Researchers try overcoming this "freak" of nature through two successive modifications. Firstly, they try devising conditions for incapsulation of chemotherapeutic agents (Pavel Plevka et al. Structure and Stability of Icosahedral Particles of a Covalent Coat Protein Dimer of Bacteriophage MS2//Protein Science 2009, v. 18 (5), pp. 1653-1661 and Jeff E. Glasgowa et al. Osmolyte-Mediated Encapsulation of Proteins inside MS2 Viral Capsids//ACS Nano. 2012 Oct. 23; 6(10): 8658-8664). Secondly, the virion surface is modified, thus endowing the MS2 bacteriophage particles with the ability to be sorbed on the surface (due to the ligand-receptor interactions) and then penetrate into the cytoplasm of a malignant cell (U.S. Pat. No. 5,534,257; US Patent Application 20130017210; Stacy L. Capehart et al. Controlled Integration of Gold Nanoparticles and Organic Fluorophores Using Synthetically Modified MS2 Viral Capsids//J Am. Chem. Soc. 2013, Feb. 27; 135(8): 3011-3016). However, the above-described researchers' efforts to create targeted delivery systems based on modified viruses are impaired because of the MST cells' genetically determined ability to remove molecules of various toxic chemotherapeutic agents from the cells (Stavrovskaya A. A., T. P. Stromskaya. Transport Proteins of the ABC Family and Multidrug Resistance of Tumor Cells//Biochemistry (Moscow), 2008, v. 73(5), pp. 592-604). The capability to remove chemotherapeutic agents from the cells is implemented by drug resistance proteins or MDR (Multidrug Resistance) proteins (Stephan Wilkens. Structure and Mechanism of ABC Transporters//F1000Prime Reports 2015, 7:14-23).

Along with this, attention should be paid to the fact that penetrating into the cytoplasm of an MST cell via channels specific to potassium ions, radioactive univalent isotope 201Tl is not subject to removal from the cytoplasm (Jean C. Maublant et al. In Vitro Uptake of Technetium-99m-Teboroxime in Carcinoma Cell Lines and Normal Cells: Comparison with Technetium-99m-Sestamibi and Thallium-201//The Journal of Nuclear Medicine November 1993, v. 34(11), pp. 1949-1952; Brismar T. et al. Increased Cation Transport in Mdr1-Gene-Expressing K562 Cells//Cancer Chemother Pharmacol. 1995; v. 36(1): pp. 87-90; M. Fukumoto et al. Scintigraphic Prediction of Resistance to Radiation and Chemotherapy in Patients with Lung Carcinoma// Cancer 1999, Oct. 15, v. 86(8), pp. 1470-1479).

Direct experiments (Spenser P S. et al., Effects of Thallium Salts on Neuronal Mitochondria in Organotypic Cord-Ganglia-Muscle Combination Cultures//The Journal of Cell Biology, 1973, v. 58(1), pp. 79-95) show that the level of toxicity of salts of univalent thallium per culture cell lies within 1 pg (for a normal line of HEK293 cells) and 40 pg (for U251 glioblastoma cells). According to X-ray structural analysis data (Ailong Ke et al. Structural Roles of Monovalent Cations in the HDV Ribozyme//Structure March 2007, v. 15(1), 281-287), interacting with genomic RNA inside an MS2 phage particle (an internal radius of 10 nm), ions of univalent thallium will achieve a concentration lethal for the cell after having absorbed 20 loaded virions. These calculations have served as a basis for creating a system for targeted delivery of thallium salts to MST cells, univalent cations of which are resistant to exposure to the MDR proteins. This invention proposes a solution for therapeutic and diagnostic needs during targeted chemotherapy of MSTs.

BRIEF SUMMARY OF THE INVENTION

This invention is aimed at creation of targeted delivery of salt of univalent thallium to MST cells and endothelium of the vessels that feed them using MS2 phage surface-modified virions filled with salts of univalent thallium.

Application for an invention (US Patent Application 2013/0251630 as well as PCT/DK2011/050479, EP 2651447A1 and CA 2821024 A1) and WO 2015061592A1 (application PCT/US2014/062007) are the closest analogues of the existing invention. Both applications expound ways of targeted delivery of metal radionuclides or pharmaceutic compositions introduced into liposomal nanoparticles to tumor cells. Unlike the said applications, however, this application expounds a way of delivering ions on univalent thallium (including radioactive one) using surface-modified particles of the MS2 bacteriophage. Ways of incorporating various toxic chemotherapeutic agents into an MS2 bacteriophage are known4; for example, in U.S. Pat. No. 6,159,728 or in US Patent Application 20100167981. However, the said references do not expound ways of incapsulation of univalent thallium into the bacteriophage or its virus-like particle and the targeted delivery of univalent thallium to MST cells.

There are known ways of targeted delivery of various chemical compounds to MST cells and their blood vessels (US Patent Application 20090246133, 20140186265, 20150004688); however, use of a surface-modified virion of an MS2 phage is not expounded for these purposes. In publications (Ruoslahti E. Specialization of Tumor Vasculature//Nat Rev Cancer 2002 February; v. 2 (2): pp. 83-90; K. N. Sugahara et al. Tissue-Penetrating Delivery of Compounds and Nanoparticles into Tumors//Cancer Cell Dec. 8, 2009, v. 16 (3), pp. 510-520) a description of a method of obtaining surface-modified virus-like particles of the MS2 phage can be found, so that they interact with receptors of MST cells and of the vessels that feed them according to the ligand-receptor mechanism. Nevertheless, these publications do not describe a method of filling such viral particles with salts of univalent thallium.

Many patents and patent applications expound methods of surface modification of an MS2 bacteriophage or its virus-like particles (U.S. Pat. Nos. 5,698,424; 5,534,257; 5,470,573; 5,698,424; US Patent Application 20090054246; US Patent Application 20140106982; US Patent Application 20130149336; RF Patent 2526570). However, all they are aimed exclusively at obtaining the specific immune reaction, including one the purpose of immunotherapy of MSTs. Such researches and patents are analogues of phage displays (Mc Cafferty J. et al. Phage Antibodies: Filamentous Phage Displaying Antibody Variable Domains//Nature 6 Dec. 1990, v. 348, pp. 552-554; U.S. Pat. No. 5,821,047; 5,702,892) and are not related to this application.

There are known ways of application of radioactive salts of thallium (201Tl, USSR Patent 1088558) as a way of diagnostics or a prognostic method of visualization of an individual's MST. Analogous foreign patents (US Patent Application 20140037541; US Patent Application 20130324847A1; U.S. Pat. Nos. 4,764,598; 4,446,123) are known. All these examples expound methods of preparing extracorporally introduced diagnostic preparations that are nontoxic for clinical application. At that, the amount of once introduced univalent thallium is 10-100 pg/kg or a 10-6 part of hLD50=1.5 mg/kg (Toxicological Review of Thallium and Compounds//U.S. Environmental Protection Agency, Washington, D.C. September 2009).

This invention in aimed at satisfying the need for targeted delivery of univalent thallium that rules out toxic exposure of the organism to the toxic substance, but guarantees destruction of an MST cell. This methodology for targeted delivery of univalent thallium has the following advantages, such as easiness of application, better detection in the MST propagation zone, effective absorption, absence of toxicity, controlled release of univalent thallium from the virion, decrease in the applied dose of thallium and simple creation of the substance. Apart from that, the substance in this invention does not irritate skin and mucous surfaces.

SUMMARY OF THE INVENTION

One of the invention aspects proposes a way of targeted delivery of salts of univalent thallium that includes preparation of MS2 phage virions or its virus-like particles with subsequently modifying their surface with cyclical ligand filled with univalent thallium salts, so that this way of preparation does not permit "effluence" of the metal ions from the virions before their physical or biochemical destruction.

In the related aspects, the invention proposes a way of targeted delivery of salts of univalent thallium isotope 201Tl.

In the preferred variant, cyclical polypeptide able to interact with MST cell receptors is the ligand, and in the most preferred variant, iRGD is the ligand. The ligand can be chemically conjugated to form covalent attachment or attached through merging with an A-protein gene sequence.

In the preferred variants, the salt of univalent thallium is chosen from the group of haloid salts, acetate, nitrate, sulphate, carbonate.

This invention proposes substance where MS2 phage virions or its virus-like particles with the surface modified by cyclical ligand are potentially able to penetrate through undamaged skin integuments.

These and other aspects of this invention will become evident with reference to the following detailed description and drawings attached. Besides this, the various references presented below, wherein some procedures are described in more detail, are included herein in full for reference. This and other aspects and variants of implementation of the invention are described below in more detail and with reference to the examples and figures attached.

BRIEF DESCRIPTION OF THE DRAWINGS

FIG. 1 A. Electrophoretic separation of MS2 phage particles: empty ones (the last track on the left) and filled with thallium partly (middle track) or to the limit (the last one on the right).

B. Electronic microphotographs of MS2 phage particles filled with TINO3. C. A microphotograph of MS2 phage particles (control). The scale line is 1 nm.

FIG. 2. The chart of effectiveness of filling MS2 phage particles with salts of univalent thallium (exemplified by TINO3). A. Filling the phage particles depending on the salt concentration in the phage stock. B. The ratio of the "introduced into the particles"/added to the stock on the salt amount.

FIG. 3. The chart of "effluence" of the salt by the example of $TlNO_3$) from the filled MS2 phage particles in time. The bottom curve are generated by $10^{10}$ MS2 phages filled with the thallium salt by the vacuum drying method with time; the upper curve are generated by $10^{10}$ MS2 phages filled with the disassembly-assembly method with time (see Example 2).

The data presented in charts 2 and 3 were analyzed using the program Statistica 12 ($p<0.01$) or Student's test.

FIG. 4. The MS2 bacteriophage's densest fraction, which contains thallium (filling through assembling-disassembling) is the heaviest one (the lower fraction), the MS2 bacteriophage fraction that contains thallium (filled through drying) is located higher, and still higher there is a wild MS2 bacteriophage fraction that does not contain thallium.

FIG. 5. Agglutination of the tumor cells exposed to MS2 phage particles with the virion's surface modified with the ligand. On the left. Cells that have grown in environment without VEGF. On the right. Cells that have grown in environment with VEGF.

FIG. 6 Penetration of MS2 phage virions filled with thallium into the cells. On the left. Cells that have grown without VEGF. On the right. Cells that have grown with VEGF (the oval inclusions in the nuclei are accumulated thallium).

DETAILED DESCRIPTION OF THE INVENTION

The proposed way can be realized on the basis of the existing technical level through the following sequence of actions.

Firstly, preparation procedures are performed; they were described, in particular, for example, in U.S. Pat. Nos. 8,367,621, 6,399,307, 6,803,379; US Patent Applications 20130343989, 20100322862, 20150044665, the performance whereof resulted in such nanoparticles that can find their application in conformity with this invention. Moreover, the nanoparticles based on nanomaterials described in U.S. Pat. No. 6,180,389 and US Patent Applications 20040028694, 20140045915, 20140314664, 20140341938 are regarded as a nucleus of the phage's modified virion, according to this invention.

Simultaneously with obtainment of high titers of the MS2 phage, chemical reactions were performed to devise an original method of synthesis of cyclical peptides used for modifying the surface of MS2 phage virions.

In some variants of the invention, the phage's modified virions may contain 201Tl radionuclide, which is usually used as salt of univalent thallium, such as chloride, iodide or bromide. Use of radionuclides as indicators of the labels is well-known in this sphere, and they can be easily adapted by a specialist in this filed for use within the framework of this invention. Radionuclides can be used when disassembling-assembling the phage's modified virions to be filled with the salts and as tags with the salts introduced.

Here transmission electron microscopy (TEM) became a method of detecting and researching the phage virions. The method of plasmon resonance (SPR) became another way of detecting the particles; its wave permits detecting the sorbed particles of the modified virions, including ones filled with thallium, on glass (V. N. Konopsky et al. Photonic Crystal Biosensor Based on Optical Surface Waves//Sensors 2013, 13(20), pp. 25662578). Fluorescent spectroscopy can be used for analyzing the samples that contain salts of univalent thallium (D I ZHANG et al. A Thallium Transport FLIPR-Based Assay for the Identification of KCC2-Positive Modulators//Journal of Biomolecular Screening 2010, v. 15 (2); pp. 177-184) in order to determine the effectiveness of its packing and elution. Besides that, the isotopic tag can be used for facilitating the detection of the ion during its packing and elution.

All the manipulations with the materials that contain thallium salts are conducted taking into account the Russian Federation Chief State Sanitary Physician's letter dated Jan. 6, 2004, No. 2510/92-04-32.

The invention is exemplified by the following:

Example 1

A high titer of the MS2 phage was obtained according to the method described earlier (Knyazhev V. A., Sivov I. G., Sergiyenko V. I. RNA Transduction by Non-Infectious Virions of the MS2 Phage//Molecular Genetics, Microbiology and Virology 2002, No. 3, pp. 56-63). Sequenation of RT-PCR of a genomic RNA fragment as well as determination of the titer using agar layers served as the control (Gratia A. Numerical Relations between Lysogenic Bacteria and Particles of Bacteriophage//Ann. Inst. Pasteur 1936, v. 57, p. 652). The phage virions were concentrated after having clarified the cell lysate through centrifugation (15000 rpm) with subsequently precipitating PEG-6000 in the presence of NaCl, as specialists know. Also, the phage preparation was concentrated by dehydrating with dry Sephadex G-10.

Example 2

Filling an MS2 phage with thallium salts and control over the process.

A. By vacuum drying, the mixture of the phage preparation with thallium solutions having been dried.

B. By disassembling-assembling: it has been performed according to a protocol known to specialists (U.S. Pat. No. 8,987,173), keeping the phage for 24 hours in ST buffer (50 mM of tris, 100 mM of NaCl) in the presence of 0.25 M of TMAO and 0.1 M of thallium salt. Then the solution was centrifuged at 10000 g for 10 minutes. The supernatant was mixed with PEG-6000 and NaCl to an end concentration of 12.5% and 0.5 M respectively. After 2 hours, the solution was precipitated by centrifuging (17800 g for 45 minutes) at 4° C. The precipitate was dissolved in a minimal amount of ST buffer and precipitated again at 10000 g for 10 minutes. The supernatant was fractionated, and the fractions that corresponded to intact capsules of the MS2 virus were collected and then stored at 4° C. in ST buffer.

C. The quality of the incapsulated thallium was controlled using the method of fluorescence with PTSA (quaternary sodium salt of pyrene-1,3,6,8-tetrasulfonic acid) (D I Zhang et al. A Thallium Transport FLIPR-Based Assay for the Identification of KCC2-Positive Modulators//Journal of Biomolecular Screening 2010, v. 1, pp. 177-184). The samples were obtained after washing the phage particles incapsulated with thallium as well as after having thermally denatured the precipitate of these particles and further treating the warmed sample with RNase.

Example 3

Comparison of the MS2 phage and its modified variants.

A. Using the method of electrophoresis in polyacrylamide gel: it was performed in conformity to a workbook (Moscow State University, Department of Bioengineering of biophage, Moscow, 2007) in 2% polyacrylamide gel with agarose under conditions known to specialists.

B. Using the method of equilibrium centrifugation in sucrose density gradient:

The sucrose density gradients from 5 to 50% (weight/volume) were formed in test tubes (Beckman Instruments, Inc., Fullerton, Calif.) according to the method (Brakke M. K. Density-Gradient Centrifugation. Methods in Virology Volume 2. Edited by: K Maramorosch and H Koprowski. New York, Academic Press; 1967:93-118). The phage sample was suspended in 1 ml of cold phosphate buffer with pH=9.0, layered on the sucrose gradient and centrifuged at 85000 g for 6 hours.

C. Using transmission electron microscopy (TEM):

Silver contrasting (45 min, Aurion, Great Britain) was used for visualization of the phage particles. After detection, it was performed with 1% (mass/volume) of osmium tetroxide in phosphate buffer for 1 hour, and the filters were washed in phosphate buffer for 10 min. The filters were taken out from the insert, and 2 segments sized at 3-5 mm×2 mm were randomly cut. These segments were dehydrated in 30-100% ethanol and, at last, put into Epon resin. Ultrathin cuts were made with a diamond Diatome knife 70-80 nm thick, which were then put onto copper meshes covered with Pioloform. The meshes were contrastingly dyed in uranyl acetate for 35 min, washed three times by submerging the meshes in lead citrate for 7 minutes and washed three times. The meshes were observed using a JEM-1400 transmission electron microscope that operated at an accelerating voltage of 80 kV at a magnification of ×8000.

D. Using the SPR method:

The surface resonance plasmon (SPR) was researched with an Eva 2.0 instrument (http://www.pcbiosen-sors.com, RF Patents 2341785, 2442142). Solution of anti-MS2 IgG (10 μm/ml) mixed with the dye N-hydroxysuccinimide ether of 5-carboxy tetramethylaminorhodamine (0.1 μM, kex=575 nm; kem=605 nm) was stored in 0.1 mM sodium acetate (pH=5.5). The standard procedure of binding the IgG with glass was conducted using 3,3-diethoxypropyl-triethoxysilane according to a previously described procedure (RF Patent 681837). The groups that had not reacted on the glass surface were blocked with 1 M ethanolamine of pH=8.5 up to the full deactivation. All the researches were made three times with a volume rate of 300 μl/min. The samples that contained the phage were diluted 1:100 and/or 1:50 in "phage" buffer. After each measurement the surface was reduced with 100 mM NaOH solution and then washed with running "phage" buffer.

The molar ratio between the IgG and dye permits evaluating the maximal amount of the protein bound with the surface of the chip by fluorescence of the dye (U.S. Pat. No. 5,800,996) that has been bound with the glass by virtue of the anti-MS2 IgG.

Example 4

Modification of the phage particles' surface with peptides.

A. Synthesis of peptides with the structure (NH2) GGGCRGDK/RGPD/EC(COOH) The peptide was synthesized using the method of solid-phase peptide synthesis proceeding from Fmoc-amino acids with an automatic peptide synthesizer 433A Applied Biosystems on resin with attached Fmoc-Cys(Acm) residuum. The following derivatives of amino acids were used: Fmoc-Cys(Acm), Fmoc-Arg(Pbf), Fmoc-Asp(OtBu), Fmoc-Gly, Fmoc-Lys(Boc), Fmoc-Pro. The Fmoc-protective group was taken off the N-end alpha amino group of the growing peptide chain using 22-percent solution of 4-methylpiperidine in N-dimethylformamide (Aleshina Ye. Yu., Pyndyk N. V., Moysa A. A., Sanzhakov M. A., Kharybin O. N., Nikolayev Ye. N., Kolesanova Ye. F. Synthesis of a Fragment of P-amyloid 5RHDSGY10 and Its Isomers. Biomed. Chemistry, 2008, v. 54, No. 2, 154-166). Amino acids were attached to the growing peptide chain (except Fmoc-Cys(Acm)) by preliminarily activating Fmoc-amino acids with hexafluorophosphate 2-(1H-benzotriazole-1-yl)-1,1,3,3-tetramethylaminium in the presence of 1-hydroxybenzotriazole and 2,4,6-collidine according to the FastMoc procedure described in the manual to the synthesizer. Fmoc-Cys(Acm) was attached with activation in situ, using diisopropylcarbodiimide in the presence of 1-hydroxybenzotriazole as an activator. After having finished the synthesis, the peptide was taken off the resin by treating it with mixture of trifluoroacetic acid, tri-(isopropyl)-silane, 3,6-dioxa-1,8-octanedithiol and water (with a volume ratio of 94:1:2.5:2.5) and precipitated using methyl tertiary butyl ether. The peptide precipitate was dissolved in 10-percent water acetonitrile with 0.1% of trifluoroacetic acid, and the obtained solution was subjected to purification using the HPLC method in a Zorbax SB-C8 column, 21.2×250 mm, 7 μm in acetonitrile concentration gradient in 0.1% water solution of trifluoroacetic acid. The fraction that contained the target peptide was collected and steamed under vacuum, and then the protective Acm-groups were removed from the cysteine residua with simultaneously forming a disulphide bridge according to a known methodology (Fernando Albericio et al. Preparation and Handling of Peptides Containing Methionine and Cysteine//In: Fmoc Solid Phase Peptide Synthesis: A Practical Approach. Eds. W. C. Chang and P. D. White. Oxford University Press, 2000). The peptide was purified once more through HPLC using the same column, and the target peptide fraction was steamed under vacuum.

B. The purity of the synthesized peptide preparation was confirmed by mass-spectrometric analysis with electropulverization ionization and detection using the ion trap method, as well as analytical HPLC in conformity with the protocols described earlier (M. H. V. Van Regenmortel, S. Muller. Synthetic Peptides as Antigens. Elsevier, 1999, pp. 88-90).

C. The peptide was conjugated the phage particles using dimethyladipimidate in conformity with a standard procedure known to specialists (M. H. V. Van Regenmortel, S. Muller. Synthetic Peptides as Antigens. Elsevier, 1999, pp. 88-90).

Example 5

Determination of sensitivity of endothelial and other cell cultures to the modified virions filled with thallium and agglutination of the cells by the modified virions.

The cell cultures of endothelial cells were obtained from the collection of the Scientific-Research Institute of Carcinogenesis of the Russian Oncologic Scientific Center and reproduced in conformity with RF Patents 2359030 and 2493251. Formation of the integrins was induced on the surface of the endothelial cells and MST cells using endothelial growth factor (VEGF), in conformity with a described procedure (RF Patent 2377017). The cells were agglutinated in conformity to a described procedure (U.S. Pat. No. 5,401,636; 5,541,417). Penetration of the MS2 phage virions filled with thallium was detected through fluorescent microscopy with PTSA dye in conformity with a procedure described earlier (RF Patent 2305270).

Example 6

Determination of sensitivity of animals to the modified virions filled with salts of univalent thallium.

The experiments were performed on 130 white noninbred rats of both sexes with a mass of 200-400 g and 263 white noninbred mice of both sexes with a mass of 17-36 g kept under vivarium conditions with a natural light regime on a standard diet (GOST R 50258-92), in conformity with methodological manuals and normative documents: GOST R 51000.3-96 and 51000.4-96; rules and International Recommendations of the European Convention for the Protection of Vertebrate Animals used for Experimental and Other Scientific Purposes (1997); laboratory practice rules (GLP) in the Russian Federation approved by the RF Healthcare Ministry's Order dated Jun. 19, 2003, No. 267.

In the first and second cases, the cumulation coefficient was calculated according to the formula: C=LD50/LD50, where LD50 is the total average lethal dose of the substance during multiple introduction; LD50 is the lethal dose of the substance during single introduction; and Ccum is the cumulation coefficient.

The invention claimed is:

1. A method for activating apoptosis of cells of malignant solid tumors in a mammal, comprising: administering a surface-modified virion of an MS2 phage containing a univalent thallium salt to the malignant solid tumor cells and their feeding vessels, wherein the surface-modified virion of the MS2 phage comprises a membrane that contains a cyclic iRGD ligand covalently attached to the membrane for targeted delivery and a core that contains genomic RNA and the univalent thallium salt, wherein penetration of the surface-modified virion into the malignant solid tumor cells is ensured by ligand-receptor interactions with avb3 and avb5 integrins, wherein the salt of the univalent thallium salt is selected from the group consisting of halides, acetates, nitrate, sulfates, carbonates and combinations thereof, wherein effluence of the univalent thallium salt from the core of the surface-modified virion of the MS2 phage does not occur until phagocytosis of the surface-modified virion of the MS2 phage has commenced.

2. The method according to claim 1, wherein the univalent thallium salt contains $^{201}$Tl.

3. The method according to claim 1, wherein the apoptosis is used to treat malignant solid tumors.

4. The method according to claim 1, wherein the targeted delivery of the univalent thallium salts to the malignant solid tumor cells is performed perorally or nasally.

* * * * *